(12) United States Patent
Beckstein et al.

(10) Patent No.: US 11,872,373 B2
(45) Date of Patent: Jan. 16, 2024

(54) DUAL FLUID INJECTION SYSTEM

(71) Applicant: Medone Surgical, Inc., Sarasota, FL (US)

(72) Inventors: Bruce Beckstein, Sarasota, FL (US); Segundo Rodriguez, Sarasota, FL (US); Erik S Brown, Sarasota, FL (US)

(73) Assignee: Medone Surgical, Inc., Sarasota, FL (US)

( * ) Notice: Subject to any disclaimer, the term of this patent is extended or adjusted under 35 U.S.C. 154(b) by 704 days.

(21) Appl. No.: 16/940,726

(22) Filed: Jul. 28, 2020

(65) Prior Publication Data

US 2021/0030957 A1     Feb. 4, 2021

Related U.S. Application Data

(60) Provisional application No. 62/880,386, filed on Jul. 30, 2019.

(51) Int. Cl.
| | | |
|---|---|---|
| *A61M 5/19* | (2006.01) | |
| *A61M 39/22* | (2006.01) | |
| *A61M 39/24* | (2006.01) | |
| *A61M 39/08* | (2006.01) | |
| *A61M 5/34* | (2006.01) | |

(52) U.S. Cl.
CPC ............... *A61M 5/19* (2013.01); *A61M 5/34* (2013.01); *A61M 39/08* (2013.01); *A61M 39/22* (2013.01); *A61M 39/223* (2013.01); *A61M 39/24* (2013.01); *A61M 2039/229* (2013.01); *A61M 2205/078* (2013.01)

(58) Field of Classification Search
CPC .......... A61M 5/19; A61M 5/34; A61M 39/08; A61M 39/22; A61M 39/223; A61M 39/24; A61M 2039/229; A61M 5/16827; A61M 5/16881; A61M 5/2066; A61M 2005/14513; A61M 5/1408; A61M 5/14526; A61M 5/2053; A61M 39/105; A61M 5/3291; A61M 5/3293; A61M 5/13293

See application file for complete search history.

(56) References Cited

U.S. PATENT DOCUMENTS

| | | | | |
|---|---|---|---|---|
| 4,044,757 | A * | 8/1977 | McWhorter | ........ A61M 5/1456 604/82 |
| 2013/0131633 | A1 * | 5/2013 | Mudd | ..................... A61M 5/19 604/506 |
| 2018/0177633 | A1 * | 6/2018 | Haffner | ................. A61F 9/0017 |

* cited by examiner

*Primary Examiner* — Theodore J Stigell
(74) *Attorney, Agent, or Firm* — Fox Rothschild LLP

(57) ABSTRACT

A dual fluid injection device is provided that includes at least two syringes. A hub is provided, to which a first syringe and a second syringe are simultaneously connected. The hub includes a fluid delivery member at an end thereof for injection at a site. The first syringe and the second syringe are actuated independently at a directional control valve.

23 Claims, 13 Drawing Sheets

DUAL FLUID INJECTION SYSTEM

CROSS-REFERENCE TO RELATED APPLICATION(S)

This application claims the benefit of priority to U.S. Provisional Application No. 62/880,386, filed on Jul. 30, 2019, the disclosure of which is hereby incorporated in its entirety by reference.

TECHNICAL FIELD

The present disclosure relates generally to a dual fluid injection system, and more particularly, to a system in which injection devices are controlled independently to administer fluid through a single channel.

BACKGROUND

The delivery of therapeutic agents in various microsurgeries requires controlled injection in what is considered to be a delicate surgical procedure. As an example of a microsurgical procedure, ophthalmic procedures require such control using a microinjection cannula or similar device to enter subretinal area of an eye. Balanced salt solution (BSS) is injected beneath the retina to create a bleb or space under the retina. The bleb is created prior to being able to deliver a gene therapy or similar agent to the subretinal area of the eye.

In general, the treatment includes creating the bleb or space under the retina by a slow, controlled injection of a solution, such as, a balanced salt solution. After the bleb is created, the therapeutic agent can be injected into the space created by the balanced salt solution. In case of injection of a gene therapy, this treatment uses a vector to insert a corrective copy of a gene into the cells having a gene defect.

Developed devices for these types of microsurgeries require the use of two separate injection means. For example, a first micro cannula coupled to a syringe is used to create the bleb by injection of the balanced salt solution. Then, a second, separate, micro cannula is used to deliver the therapeutic agent into the bleb. However, this process requires two separate entries into the eye. At the second insertion, the surgeon is required to locate the micro hole that was created by the first injection in an attempt to enter the same hole. Inevitably, this increases the risk of stretching the retina entry hole and may potentially cause damage to the injection site and surrounding areas thereby decreasing the potential effectiveness of the therapeutic agent. Overall, the procedure is cumbersome requiring an exchange of instruments and requires substantial precision in a delicate surgical procedure.

Accordingly, there is a demand for the development of an improved injection system that reduces the number of injections into the eye and prevents further damage thereto during microsurgical procedures.

The above information disclosed in this Background section is only for enhancement of understanding of the background of the invention and therefore it may contain information that does not form the prior art that is already known to a person of ordinary skill in the art.

SUMMARY

According to various embodiments, the present disclosure provides a dual fluid injection device that includes at least two syringes and a hub to which a first syringe and a second syringe are simultaneously connected. The hub includes a fluid delivery member at an end thereof for injection at a site. Additionally, the first syringe and the second syringe are actuated independently at a directional control valve. The first syringe is releasably connected directly to the hub and the second syringe is releasably connected to the hub via tubing.

In some embodiments, the syringes are releasably coupled to a pneumatic drive system. In particular, each of the first syringe and the second syringe may be driven pneumatically to actuate a stopper disposed within each syringe. In addition, the first syringe is connected to a first one-way check valve that is integrated in the hub to prevent back flow of fluid into the first syringe. The system further includes a second one-way check valve disposed between the second syringe and the hub to prevent back flow of fluid into the second syringe.

Further, each of the first syringe and the second syringe is connected to a first releasable connector and a second releasable connector, respectively. The directional control valve is connected to the first releasable connector of the first syringe and the second releasable connector of the second syringe via tubing. In addition, the directional control valve is releasably connected to an external pneumatic pump via a connector. The directional control valve is further connected to the connector via tubing. Particularly, the directional control valve may be user operated to select one of the first syringe and the second syringe for actuation.

In additional embodiments, fluid contained in each of the first syringe and the second syringe is injected through fluid delivery member via the hub. Each of the first syringe and the second syringe may include a different fluid. The first syringe may contain a therapeutic agent and the second syringe may contain a balanced salt solution. The fluid delivery member may be a cannula, a needle, or a catheter. A tip of the fluid delivery member may have an outer diameter range of about 0.13 mm to 0.10 mm or less and may be made of a flexible polyimide material. Additionally, the directional control valve may be operated manually or electronically to regulate fluid flow to each of the first syringe and the second syringe.

Notably, the present invention is not limited to the combination of the device elements as listed above and may be assembly in any combination of the elements as described herein.

Other aspect of the invention as disclosed infra.

BRIEF DESCRIPTION OF THE DRAWINGS

The above and other features of the present disclosure will now be described in detail with reference to certain exemplary embodiments thereof illustrated in the accompanying drawings which are given herein by way of illustration only, and thus are not limitative of the present disclosure, and wherein.

Figure 1:
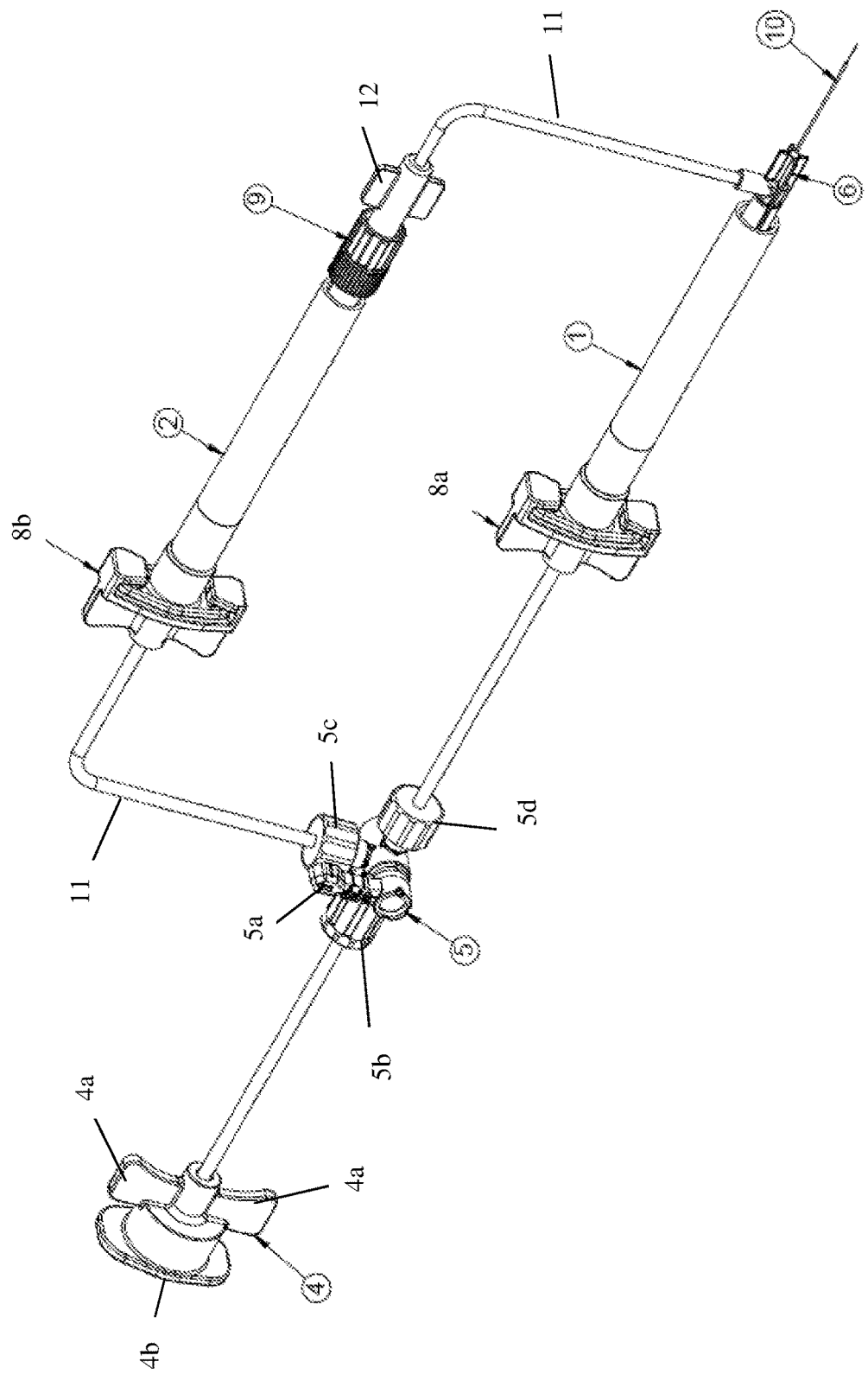
FIG. 1 is an isometric view of a dual injection device according to an exemplary embodiment of the present disclosure.

It should be understood that the appended drawings are not necessarily to scale, presenting a somewhat simplified representation of various preferred features illustrative of the basic principles of the disclosure. The specific design features of the present disclosure as described herein, including, for example, specific dimensions, orientations, locations, and shapes will be determined in part by the particular intended application and use environment.

In the figures, reference numerals refer to the same or equivalent parts of the present disclosure throughout the several figures of the drawing.

DETAILED DESCRIPTION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Advantageously, the present disclosure is capable of providing a controlled fluid injection system wherein multiple fluids are injected using a single device thus preventing the need for multiple distinct injections at a site. The present disclosure provides substantial improvements to medical procedures and specifically to microsurgical procedures, but is not limited thereto. That is, the present disclosure may be used in any application requiring multiple fluid deliveries to a site in a controlled manner. Notably, the discussion below describes the present disclosure as it relates to a subretinal surgical procedure (e.g., ophthalmic procedures) but this is merely exemplary.

Referring to FIG. 1, a dual fluid injection device according to an exemplary embodiment of the present disclosure may include at least two syringes 1, 2; a hub 6 to which the syringes are connected simultaneously; and a directional control valve 5. Notably, the present disclosure is not limited to two syringes. The device may be releasably connected via a connector 4 to an external pneumatic pump. That is, an opening end 4b of the connector 4 may be connected to a pneumatic system used to actuate the syringes. The connector may further include wings 4a between which tubing 11 extends toward the directional control valve 5.

The directional control valve 5 may include at least three openings (5b, 5c, 5d) to provide communication between the pneumatic pump and the syringes via tubing 11. Notably, the number of openings is not limited to three and may be varied based on the number of syringes designed for the system. Each opening or entry point of the valve may include a threaded connector that provides a sealed connection or flow path between the tubing and the valve. The directional control valve 5 may further include a handle 5a. The handle 5a may be user operated to adjust the flow path of fluid within the tube. For example, the openings 5c, 5d may be opened or closed based on the rotation of the handle 5a to direct the fluid within the tubing to one of the syringes. Optionally, the handle 5a may be operated electronically.

The directional control valve 5 is then connected to each of the syringes via tubing 11 and a releasable connector 8. In particular, the opening 5d may be connected to a first releasable connector 8a of a first syringe 1 via tubing 11 and the opening 5c may be connected to a connector 8b of a second syringe 2 via tubing 11. The releasable connectors allow the syringes to be disconnected from the system. A detailed description of the connector will be described herein below with reference to FIG. 3A.

As mentioned, both of the syringes are connected simultaneously to a hub 6. Particularly, the first releasable connector 8a is connected to the first syringe 1 which is then connected directly to the hub 6. The second releasable connector is connected to the second syringe 2 which is connected to the hub 6 via a second one-way check valve 9 and tubing 11. The check valve 9 in line between the second syringe 2 and the hub 6 prevents back flow of fluid flowing through the tubing. For example, the check valve prevents fluids from flowing back into the syringe which would otherwise undesirably mix different fluids contained in the syringes. Further details of the one-way check valve 9 will be described herein below with reference to FIG. 3B. The hub 6 is then connected to a fluid delivery member 10 through which the fluid is injected into a surgical site.

Figure 2:
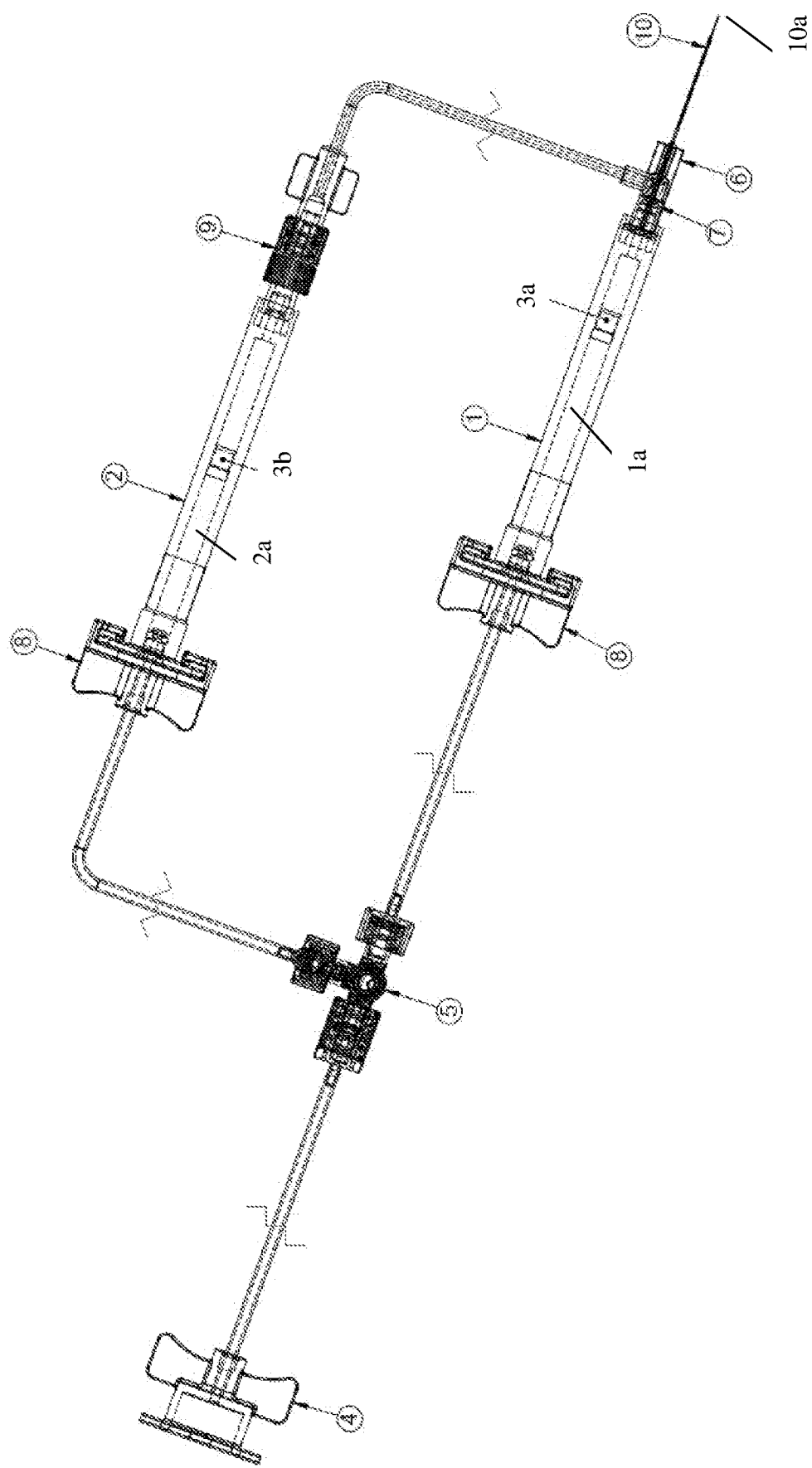
FIG. 2 is a front view of a dual injection device according to an exemplary embodiment of the present disclosure.

Reference will now be made to FIG. 2 to describe the process of injecting fluid to an injection site using the device of the present disclosure. The actuation of the fluid flow toward an injection site may be initiated by an external pneumatic system, as described above. For example, the syringes may be indirectly connected to an air pump. Since such an air pump is commonly known to those of ordinary skill in the art, a detailed description thereof will be omitted. The air pump, and in turn, the release of the fluid toward the injection side may be operated by a foot pedal or other similar operational device to control the injection flow rate. In other words, the injection flow rate is controlled by adjusting the air pressure that is used to drive the syringe plunger or stopper 3a, 3b.

In particular, each of the first syringe 1 and the second syringe 2 includes a stopper 3a, 3b disposed within the cylindrical body 1a, 2a of the syringes, respectively. Each stopper slides axially within the cylindrical body of the syringe and has a circumference that adjoins the inner wall of the cylindrical body in a sealing manner. The pressure received through the tubing from the pneumatic pump causes the sliding movement of the stoppers to then push the fluid therein out through the outlet of the syringe and toward the fluid delivery member. The syringes may be filled with about 0.15 to 25 ml of fluid, and more preferably, about 1 ml of fluid for microsurgical procedures. However, this is merely exemplary and the present disclosure is not limited thereto.

In addition to the stoppers being actuated by the pneumatic system, the directional control valve 5 determines which of the first and second stoppers will be actuated by opening the flow passage toward a desired syringe. For example, a user may manually rotate the valve handle 5a toward a desired flow passage of one of the syringes. The two syringes may contain different fluids that are to be administered sequentially. Thus, by rotation of the handle 5a, one of the flow passages may be opened while the other is blocked.

In an ophthalmic gene therapy procedure, the first syringe 1 may contain a gene therapy agent (or other therapeutic agent) and the second syringe 2 may contain a balanced salt solution (BSS). In this scenario, the valve handle 5a may be first rotated toward the second syringe 2 to inject the BSS at the injection site. This creates a reservoir, also known as a bleb. This type of space in an ophthalmic procedure is created under the retina of an eye. Once the BSS is injected to create the bleb, the valve handle 5a may be rotated toward the first syringe 1 to administer the gene therapy into the space created by the BSS. Thus, a surgeon is capable of performing what is typically two separate injections in one simplified process by administering two separate fluids through one channel and one injection site. Notably, the present disclosure is not limited as to which syringe contains the therapeutic agent and either of the syringes may contain either of the BSS or the therapeutic agent.

Figure 3A:
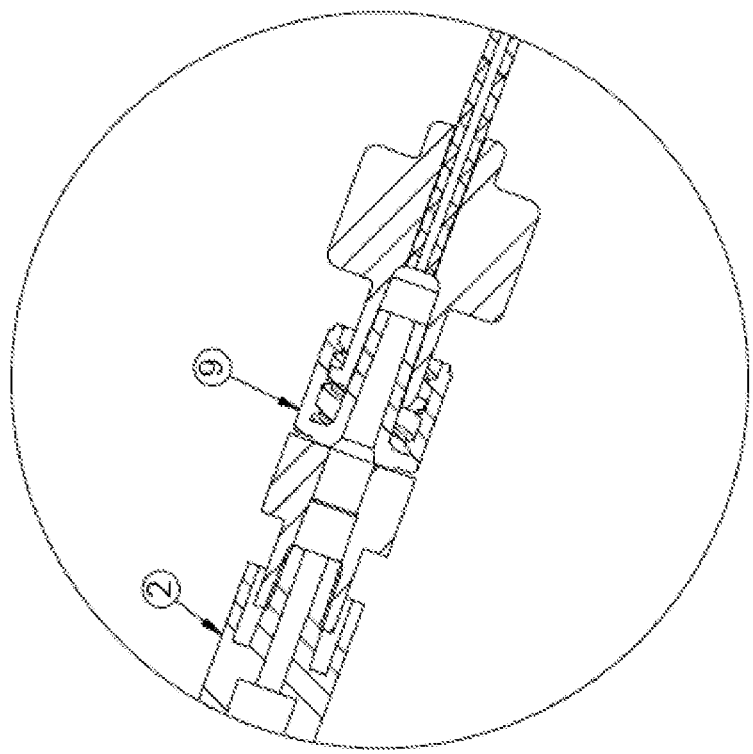
FIG. 3A is a detailed view of a releasable connector coupled to a syringe of the dual injection device according to an exemplary embodiment of the present disclosure.

To further describe the connections to the hub, reference will be made to FIGS. 2 and 3A-3C. First, the first syringe 1, as mentioned, may be connected to the first releasable connector 8a and the second syringe 2 may be connected to the second releasable connector 8b as shown in FIG. 3A. Each connector 8a, 8b may include a C-shaped projection 8c configured to mate with a flange 1c, 2c of each of the first syringe 1 and the second syringe 2. The tubing connected through the releasable connectors thus provides a flow passage into the syringes.

Figure 3B:
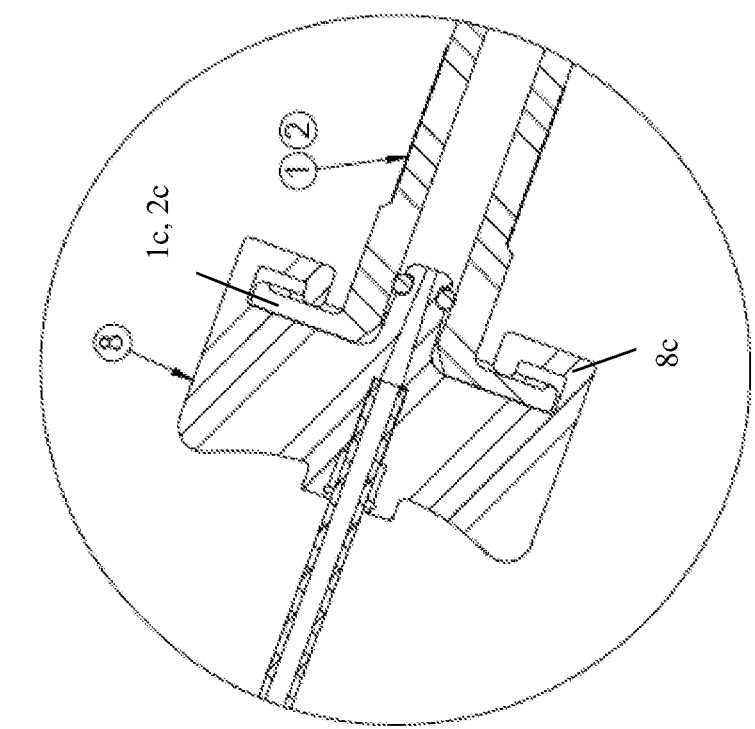
FIG. 3B is a detailed view of a one-way check valve coupled to a syringe of the dual injection device according to an exemplary embodiment of the present disclosure.

The second syringe 2 is then connected at a distal end thereof to a second one-way check valve 9. As shown in FIG. 3B, the connection between the check valve 9 and the second syringe 2 may be a threaded connection, but the present disclosure is not limited thereto. The threaded connection provides a releasable connection between the syringe 2 and the check valve 9. In particular, the check valve 9 is disposed in the fluid flow path and sealingly overlays the opening of the syringe 2 (e.g., sealingly engages the outside of the syringe opening). In response to high injection fluid pressure, the check valve 9 is pushed away from that sealing engagement across the syringe opening to open the flow passage. This adjustable sealing engagement allows for the fluid to flow in only one direction, towards the fluid delivery member and thus prevents the fluid from flowing back into the syringe and minimizes waste of the drug administered from the first syringe 1.

Figure 3C:
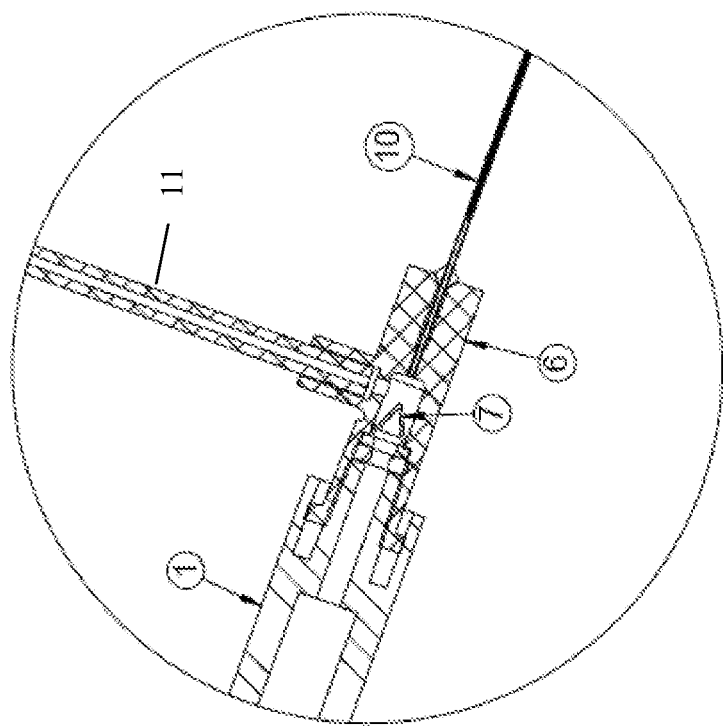
FIG. 3C is a detailed view of a hub in communication with a plurality of syringes and a fluid delivery member according to an exemplary embodiment of the present disclosure.

The second one-way check valve 9 is then connected to the tubing 11 via a tubing connector 12. That is, the check valve 9 is disposed between the syringe 2 and the tubing connector 12 to provide a continuous flow path for the fluid contained within the second syringe 2. The tubing 11 then connects to the hub 6 as shown in FIG. 3C. This provides a configuration in which the syringe containing, for example, the BSS is kept away from the surgical site for ease of use of the system. Notably, the check valve 9 is not limited to such a particular location and another positioning of the check valve 9 will be described below with reference to FIGS. 4-6.

Further, as discussed above, the first syringe 1 is connected to a first releasable connector 8a and then the distal end of the first syringe 1 is connected directly with the hub 6. This direct coupling minimizes dead space or waste of the drug or therapeutic agent contained within the syringe. This also allows for more accuracy and control over the administration of the drug delivery. In particular, as shown in FIG. 3C, a first one-way check valve 7 is integrated with the hub 6 to minimize dead space and fluid loss of the therapeutic agent contained in the first syringe 1. The inlet of the first one-way check valve 7 may be shaped to receive the outlet end of the syringe 1 in a manner that permits application of sufficient inward fluid pressure to the check valve to ensure opening thereof and to thus allow the fluid from the first syringe 1 to enter the fluid flow passage toward the fluid delivery member 10. As shown in FIG. 3C, the hub thus includes three openings to receive the first syringe, the tubing connected to the second syringe, and to connect with the fluid delivery member. However, the number of openings is not limited thereto and may be adjusted depending on the number of syringes coupled to the system.

Figure 4:
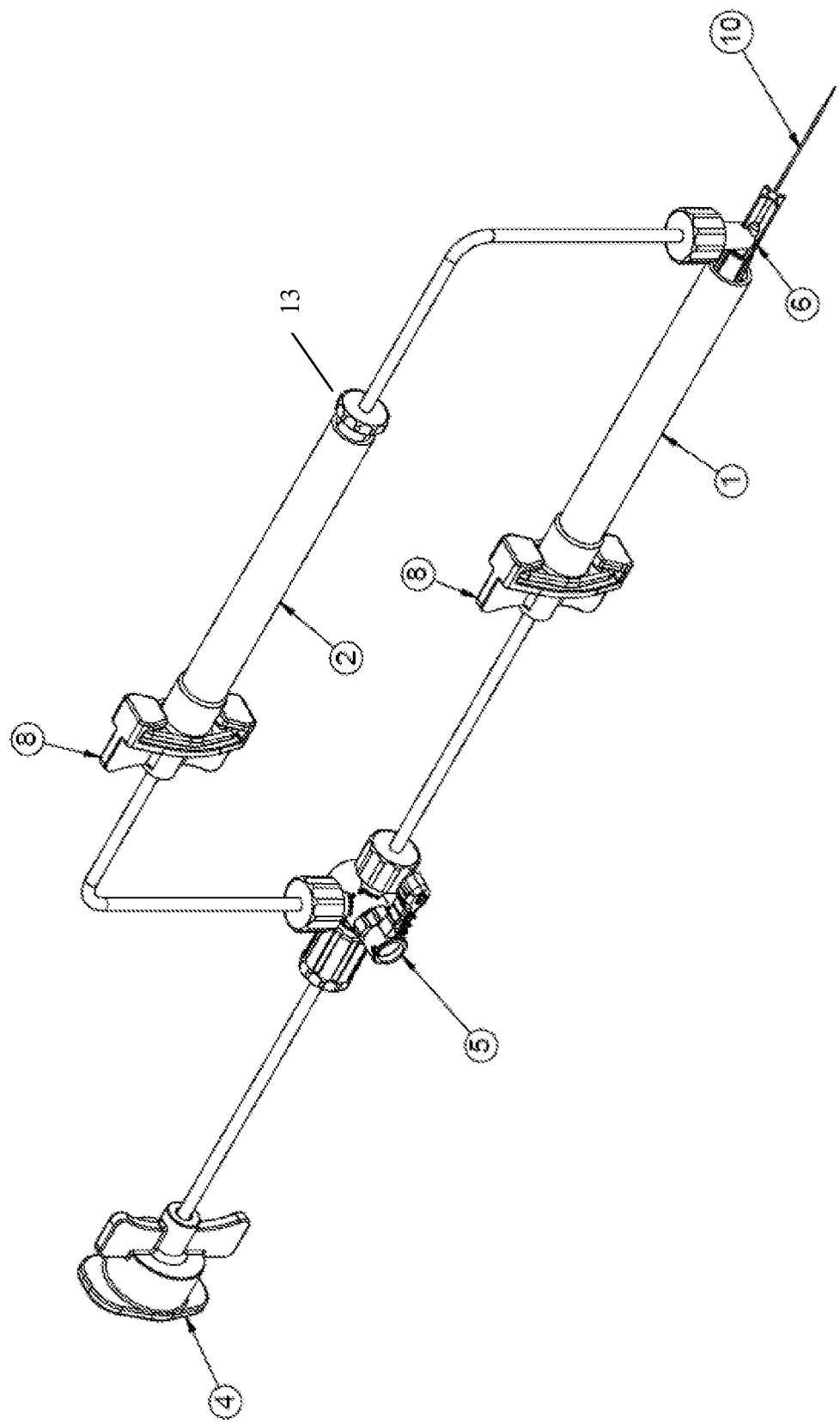
FIG. 4 is an isometric view of a dual injection device according to a second exemplary embodiment of the present disclosure.
Figure 5:
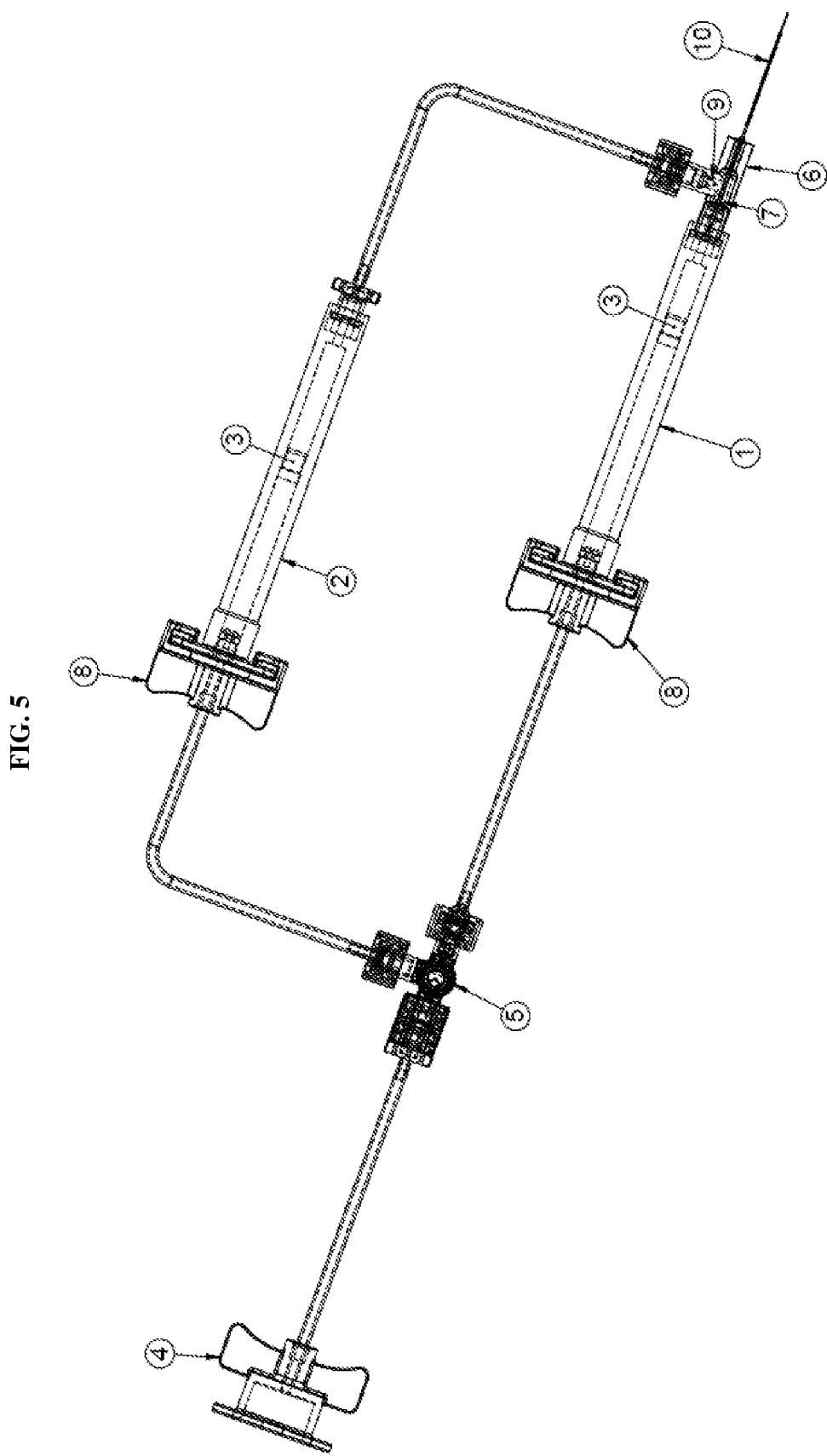
FIG. 5 is a front view of a dual injection device according to the second exemplary embodiment of the present disclosure.
Figure 6:
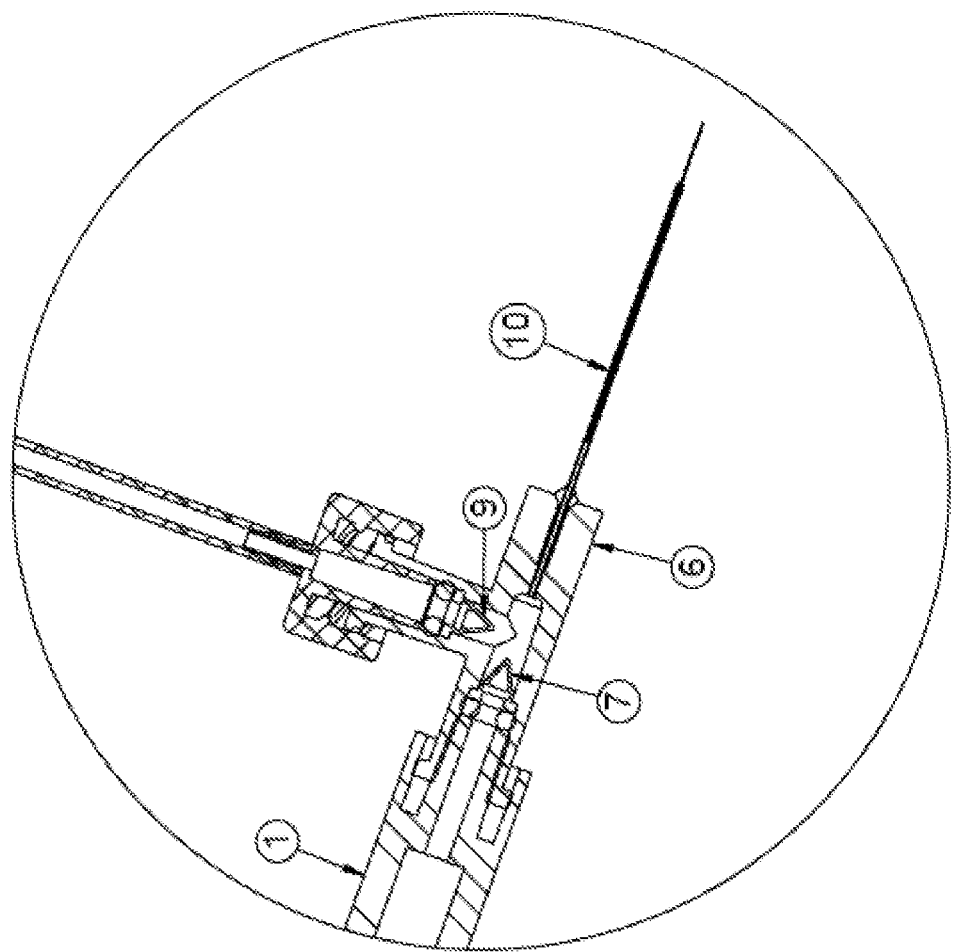
FIG. 6 is a detailed view of a hub in communication with a plurality of syringes and a fluid delivery member according to the second exemplary embodiment of the present disclosure.
Figure 7:
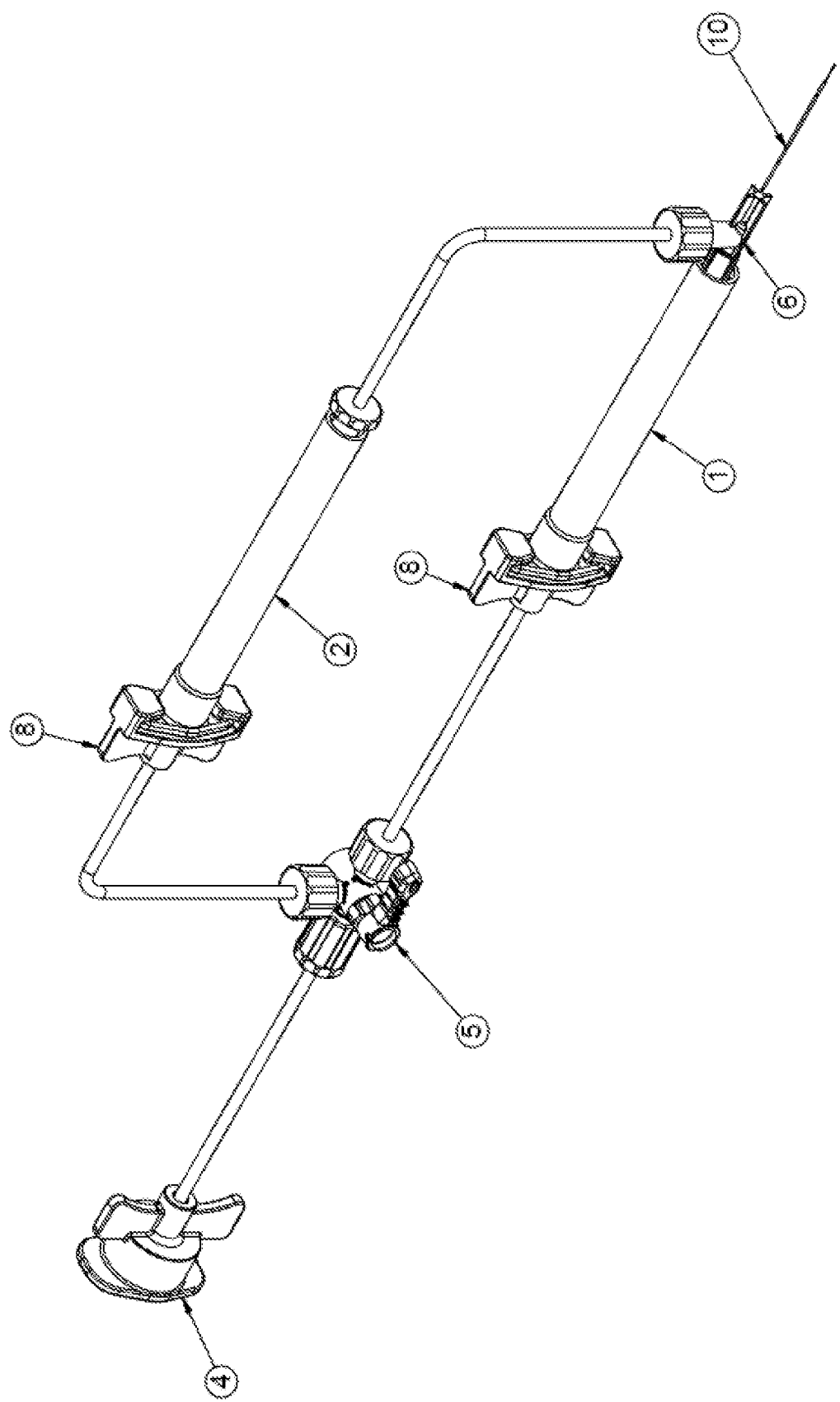
FIG. 7 is an isometric view of a dual injection device with an added cannula tip according to an exemplary embodiment of the present disclosure.
Figure 8:
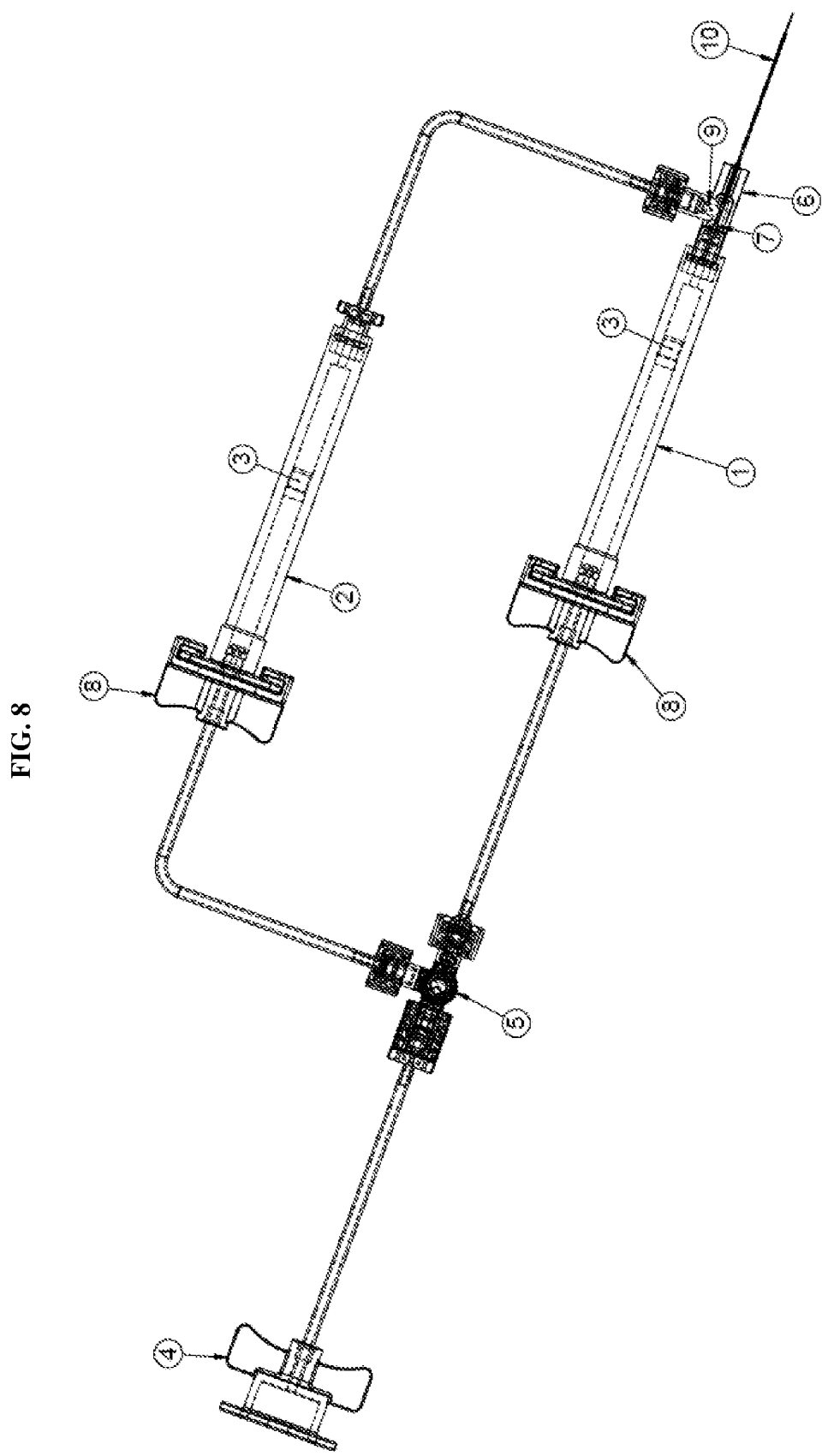
FIG. 8 is a detailed view of the dual injection device of FIG. 7 according to an exemplary embodiment of the present disclosure.
Figure 9:
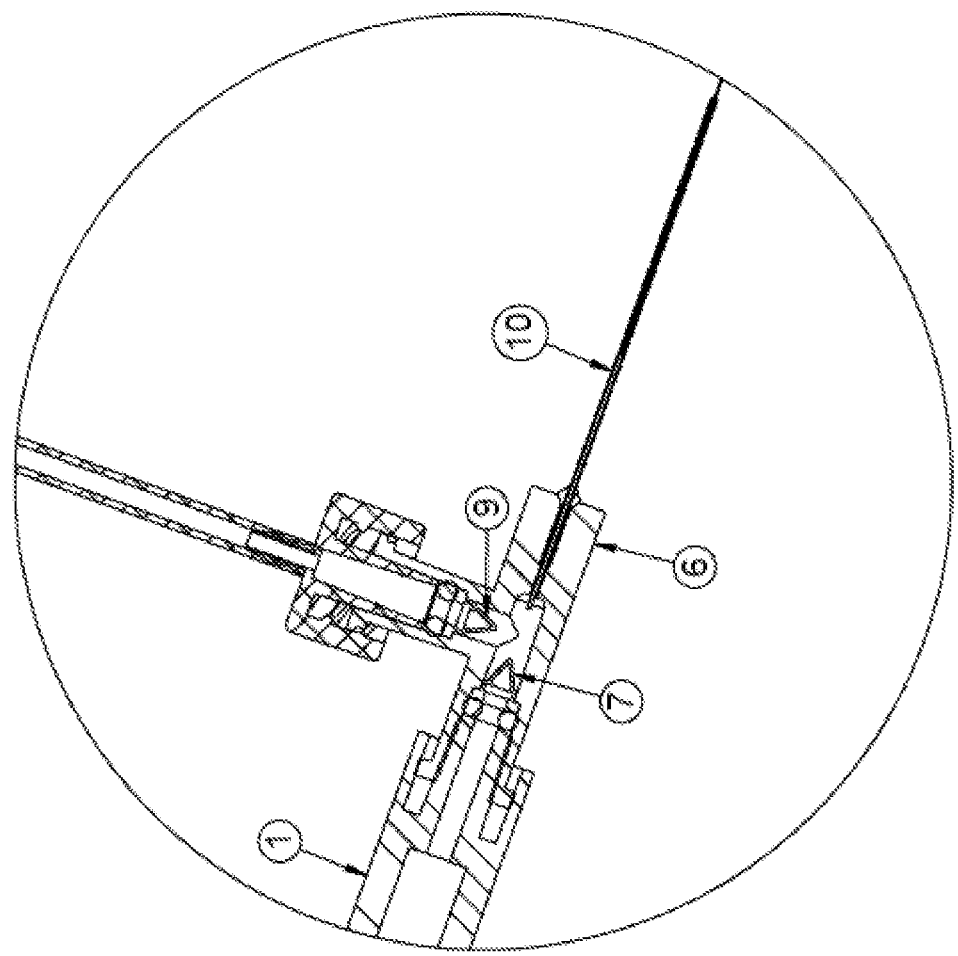
FIG. 9 is a detailed view of the a hub of FIG. 7 according to an exemplary embodiment of the present disclosure.

According to an second exemplary embodiment of the present disclosure, as shown in FIGS. 4-6, the second one-way check valve 9 may also be integrated with the hub 6. For example, the first one-way check valve 7 may be integrated at a first opening of the hub 6 in direct communication with the first syringe 1 and the second one-way valve 9 may be integrated at a second opening of the hub 6 in communication with the second syringe 2 via the tubing. In this configuration, the distal end of the second syringe is connected to a luer connector 13. The configuration shown in FIG. 6 further prevents any potential fluid from backing up the flow path to the second syringe 2. The integration of the second one-way check valve 9 with the hub 6 is similar to that described in regards to the first one-way check valve 7 and thus repeated description thereof will be omitted.

Each of the syringes is then finally connected to a fluid delivery member 10 within or through the hub 6, as shown in FIG. 3C. The fluid delivery member 10 may be one of any number of delivery devices. For example, the fluid delivery member may be a cannula, a needle, a catheter, or similar device. Since the claimed system is configured for use in microsurgical procedures, the fluid delivery device is typically a micro-member. For example, a micro-cannula may be used. In the exemplary procedure discussed herein for subretinal injections, a cannula may be provided with a tapered design having a small gauge tip. Such a design may be used with any of the above-described fluid delivery members. The tip of the fluid delivery member may be formed with an outer diameter in the range of about 0.13 mm to 0.10 mm or smaller. Additionally, the tip may be made of a flexible polyimide, metal, or other similar material. As shown in FIG. 2, the tip 10a of the fluid delivery member 10 may be inserted at an injection site and may serve as the flow passage for the fluid contained in both the first and second syringes 1, 2. Accordingly, two separate fluids may be more easily administered to an injection site using as single flow passage.

Figure 10A:
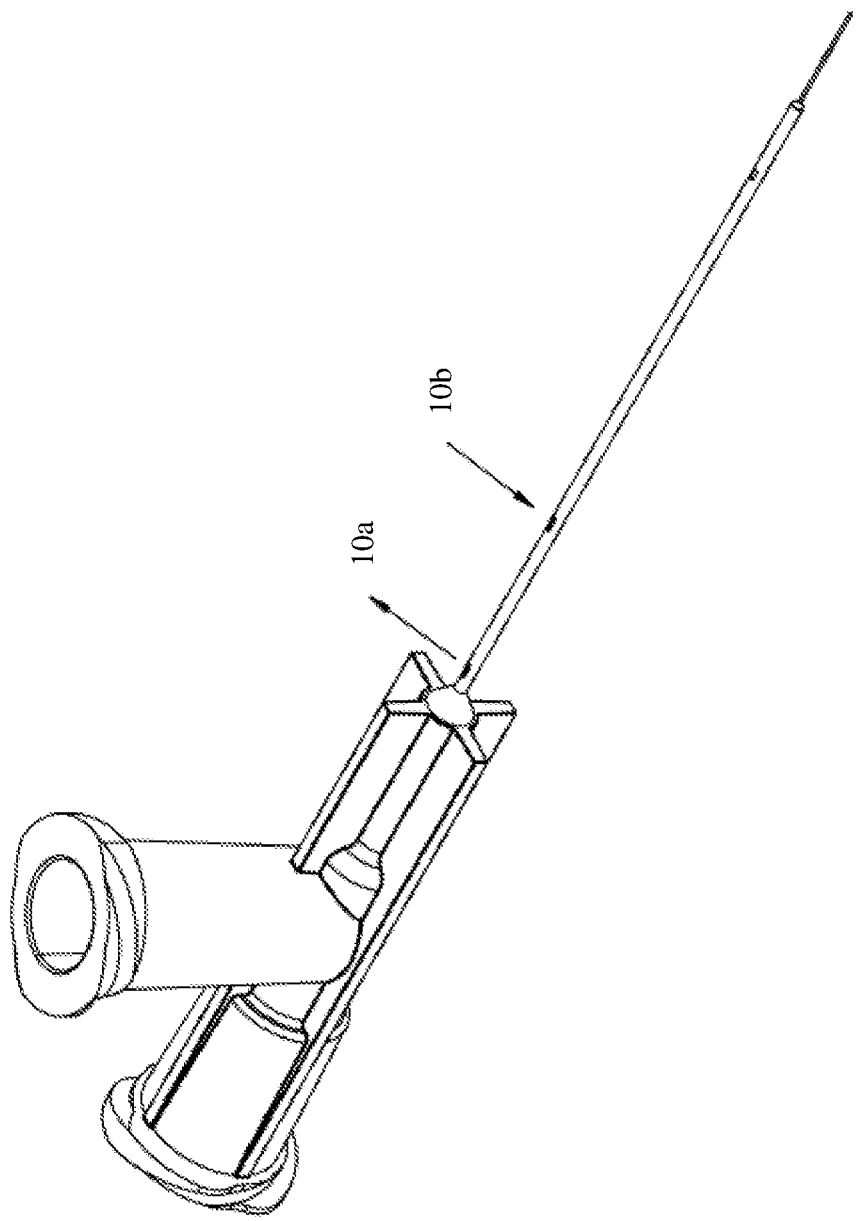
FIGS. 10A-10C are views of the cannula tip of FIG. 7 according to an exemplary embodiment of the present disclosure.
Figure 10B:
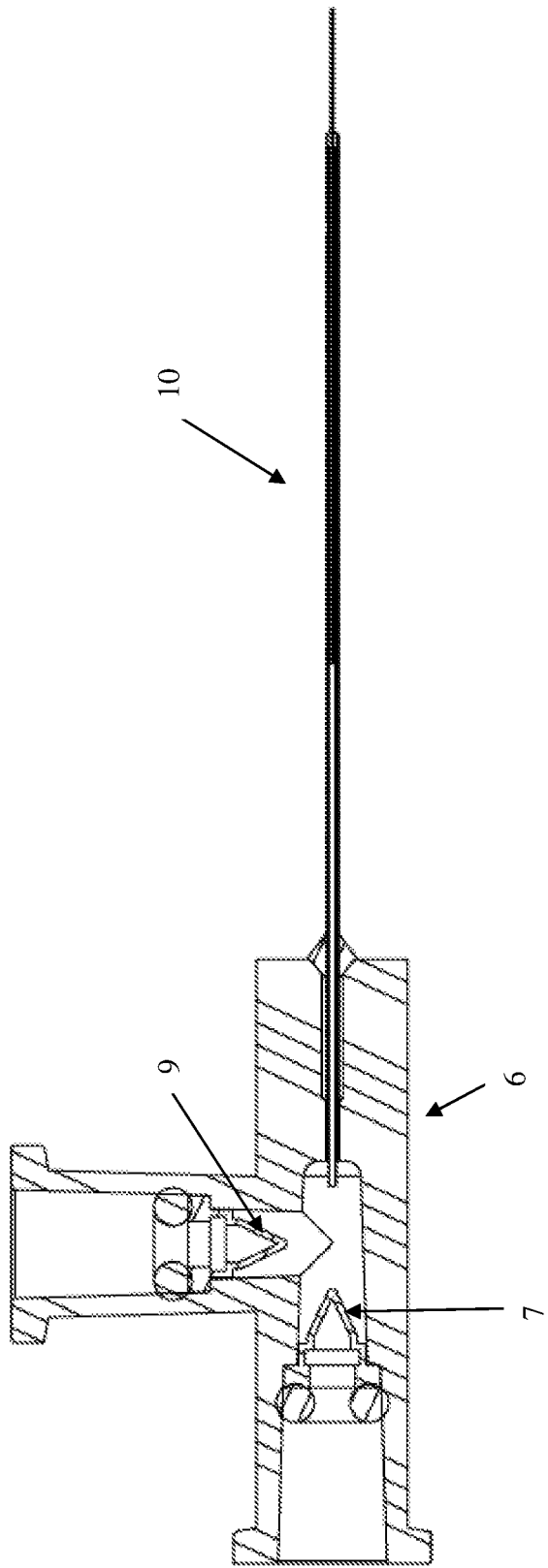
Figure 10C:
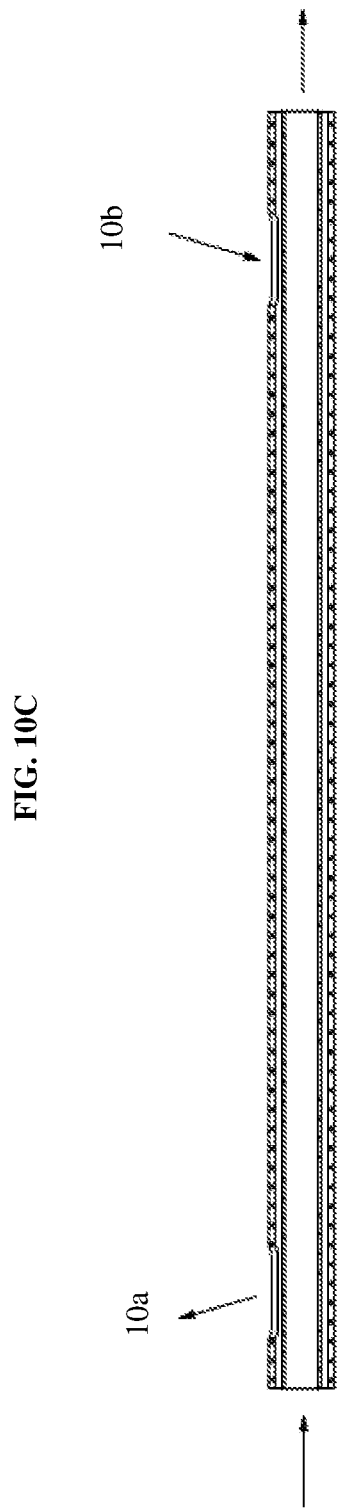

Moreover, FIGS. 7-10C illustrate a dual fluid injection device in which the fluid delivery member 10 is a cannula tip. In particular, the cannula tip may be a vented injection cannula. This configuration allows fluid to be injected through a center lumen, while vent holes and a fluidically isolated secondary channel within the shaft provide pressure relief. As shown in FIGS. 10A and 10C, the outer lumen within the shaft includes multiple vent holes 10a, 10b, one allowing fluid ingress and one fluid egress. For example, in a surgical procedure, the distal port of the cannula tip is inserted within a surgical site and allows fluid to flow there into and the proximal port is extraneous to the surgical site thus allowing fluid egress and releasing any pressure. Such a configuration is useful in a variety of surgical procedures, such as, retinal surgery where the cannula tip is injected into a fluid filled cavity where the vent hole at the proximal port allows for the fluid to be drawn out of the cavity to thus relieve pressure.

As shown in FIG. 10B, the cannula may include two coaxial lumens (defined by an inner shaft and an outer shaft) that are mounted to the hub to allow connection of the device to a syringe or other apparatus for injection of fluid. The outer shaft may include the plurality of vent holes along a length thereof and the tip of the shaft may be closed. Thus, the lumen may extend through the outer shaft but not through the tip. The inner shaft may extend distally inside the cannula of the outer shaft with one end terminating at or near the injection port. The tip of the cannula may be injected at a surgical site and fluid may be conveyed via the inner shaft through the injection port while simultaneously conveying fluid outside of the surgical site via the lumen of the outer cannula. Accordingly, this configuration prevents damage to an injection site and surrounding areas during injection of a fluid by simultaneously relieving pressure at the surgical site.

Advantageously, a desired dosage of a therapeutic agent or drug may thus be delivered in a more controlled and accurate manner. This system thus allows administration of multiple fluids through a same entry point (e.g., retina site) and reduces any potential stretching of an injection site and prevents potential contamination or other negative impacts to delicate areas during a surgical procedure.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

What is claimed is:

1. A dual fluid injection device, comprising:
   at least two syringes;
   a hub to which a first syringe and a second syringe of the at least two syringes are simultaneously connected, wherein the hub includes a fluid delivery member at an end thereof for injection at a site,
   wherein the first syringe and the second syringe are actuated independently at a directional control valve; and
   wherein the first syringe is releasably connected directly to the hub.

2. The device of claim 1, wherein the second syringe is releasably connected to the hub via tubing.

3. The device of claim 2, wherein the first syringe is connected to a first one-way check valve integrated in the hub that prevents back flow of fluid into the first syringe.

4. The device of claim 3, further comprising:
   a second one-way check valve disposed between the second syringe and the hub to prevent back flow of fluid into the second syringe.

5. The device of claim 3, further comprising:
   a second one-way check valve integrated in the hub and disposed in a flow path of the tubing to the second syringe.

6. The device of claim 1, wherein the first syringe and the second syringe are releasably coupled to a pneumatic drive system.

7. The device of claim 1, wherein each of the first syringe and the second syringe is driven pneumatically to actuate a stopper disposed within each syringe.

8. The device of claim 1, wherein each of the first syringe and the second syringe is connected to a first releasable connector and a second releasable connector, respectively.

9. The device of claim 8, wherein a directional control valve is connected to the first releasable connector of the first syringe and the second releasable connector of the second syringe via tubing.

10. The device of claim 9, wherein the directional control valve is releasably connected to an external pneumatic pump via a connector.

11. The device of claim 10, wherein the directional control valve is connected to the connector via tubing.

12. The device of claim 1, wherein the directional control valve is user operated to select one of the first syringe and the second syringe for actuation.

13. The device of claim 1, wherein fluid contained in each of the first syringe and the second syringe is injected through the fluid delivery member via the hub.

14. The device of claim 13, wherein each of the first syringe and the second syringe includes a different fluid.

15. The device of claim 14, wherein the first syringe contains a therapeutic agent and the second syringe contains a balanced salt solution.

16. The device of claim 1, wherein the fluid delivery member is a cannula, a needle, or a catheter.

17. The device of claim 16, wherein the fluid delivery member is a vented injection cannula including a plurality of holes along an outer shaft thereof.

18. The device of claim 17, wherein the tip is made of a flexible polyimide material.

19. The device of claim 16, wherein the fluid delivery member includes a tip having an outer diameter range of about 0.13 mm to 0.10 mm or less.

20. The device of claim 1, wherein the directional control valve is manually operated to regulate fluid flow to each of the first syringe and the second syringe.

21. The device of claim 1, wherein the directional control valve is electronically operated to regulate fluid flow to each of the first syringe and the second syringe.

22. A dual fluid injection device, comprising:
   at least two syringes;
   a hub to which a first syringe and a second syringe of the at least two syringes are simultaneously connected, wherein the hub includes a fluid delivery member at an end thereof for injection at a site, wherein the first syringe and the second syringe are actuated independently at a directional control valve, and wherein the first syringe is connected to a first one-way check valve integrated in the hub that prevents back flow of fluid into the first syringe; and a second one-way check valve disposed between the second syringe and the hub to prevent back flow of fluid into the second syringe, wherein the second one-way check valve is integrated in the hub.

23. A dual fluid injection device, comprising:

at least two syringes;

a hub to which a first syringe and a second syringe of the at least two syringes are simultaneously connected, wherein the hub includes a fluid delivery member at an end thereof for injection at a site, wherein the first syringe and the second syringe are actuated independently at a directional control valve;

wherein each of the first syringe and the second syringe is connected to a first releasable connector and a second releasable connector, respectively; and wherein a directional control valve is connected to the first releasable connector of the first syringe and the second releasable connector of the second syringe via tubing.

* * * * *